(12) United States Patent
Brady et al.

(10) Patent No.: US 7,405,332 B2
(45) Date of Patent: Jul. 29, 2008

(54) CHEMICAL PROCESS

(75) Inventors: Frank Brady, London (GB); Sajinder Luthra, London (GB); Yongjun Zhao, London (GB)

(73) Assignee: Hammersmith Imanet Ltd., London (GB)

( * ) Notice: Subject to any disclaimer, the term of this patent is extended or adjusted under 35 U.S.C. 154(b) by 116 days.

(21) Appl. No.: 10/528,645

(22) PCT Filed: Sep. 18, 2003

(86) PCT No.: PCT/GB03/04026

§ 371 (c)(1), (2), (4) Date: Nov. 18, 2005

(87) PCT Pub. No.: WO2004/029006

PCT Pub. Date: Apr. 8, 2004

(65) Prior Publication Data

US 2006/0106219 A1 May 18, 2006

(30) Foreign Application Priority Data

Sep. 27, 2002 (GB) ................... 0222426.9

(51) Int. Cl.
*C07C 17/00* (2006.01)
*C07C 19/08* (2006.01)
*C07C 213/00* (2006.01)
*C07F 7/08* (2006.01)
*C07D 257/00* (2006.01)

(52) U.S. Cl. ............. 570/162; 556/454; 548/253; 546/16; 546/124; 564/293

(58) Field of Classification Search ................ None
See application file for complete search history.

(56) References Cited

U.S. PATENT DOCUMENTS 5,210,247 A  5/1993  Haberle et al. ............. 556/436
5,536,732 A  7/1996  Lesur et al. ................ 514/317

FOREIGN PATENT DOCUMENTS

JP  02290885  11/1990

OTHER PUBLICATIONS

Oh et al. Comparison of [18F] Fluoropropylating Agents for 18F-Radiolabeling of Amines. Bulletin of the Korean Chemical Society, 2000, vol. 21 (11), pp. 1162-1164.*
Comagic et al. Efficient Synthesis of 2-bromo-1-[18F] fluoroethane and its application in the automated preparation of 18F-fluoroethylated compounds. Applied Radiation and Isotopes, 2002, vol. 56, pp. 847-851.*
Zhang, M-R, et.al., "Development of an Automated System for Synthesizing F-labeled Compounds Using [F]fluoroethyl Bromide as a Synthetic Precursor" Applied Radiation and Isotopes, Pergaon Press Ltd., Exeter, GB, vol. 57, No. 3, Sep. 2002, pp. 335-342.

E.S. Alexander, et.al., Polyfluoroalkyl Compounds of Silicon. Part IX. Silanes containing the Bis(trifluoromethyl)amino-group >> J. Chem. Soc. A., 1970, pp. 2285-2291.
Dietmar Seyferth, et.al., "Halomethyl-metal compounds. Phenyl(fluorodibromomethyl)mercury, a fluorobromacarben precursor" J. Organomet. Chem., vol. 51, 1973, pp. 77-87.
Edmund K.S. Liu, et.al., Fluorinationo f dimethylmercury, tetramethylsilane and tetramethylgermanium J. Organomet., Chem., 1978, pp. 167-182.
Roger L. Scholl, et al., "Silicon-29 Chemical shifts of Organosilicon Compounds" J. Am. Checm. Soc., vol. 94, No. 18, 1972, pp. 6376-6385.
D. Cooper, et.al., "Polyfluoroalkyl Compounds of Silicon. VIII Reactions of Silanes with Vinyl Fluoride and with 1-Chloro-2-fluoroethylene" J. Chem. Soc. A., vol. 196, 1967, pp. 2098-2103.
J. Vcelak, et.al., The Exchange of Fluorine in (gamma-fluoropropyl)trialkylsilanes and n-heypyl fluoride for halogens of grignard reagents Collection Czechoslov. Chem. Commun., vol. 41, 1976, pp. 131-139.
J. Vcelak, et.al, "19F-NMR spectra of (Fluoroalkyl)-substituted Silates" Collection Czechslov., Chem. Commun., vol. 41, 1976, pp. 386-390.
V.B. Puchnarevic et.al., Synthesis of gamma-fluoropropyl Substituted Silanes, Collection Czechoslov., Chem. Commun., vol. 39, 1974 pp. 2616-2620.
CAPLUS Abstract Accession No. 1999:304473 & Journal of Organic Chemistry vol. 64, No. 12, 1999, Ung chan Yoon, et.al, "A Solvent Effect that Influences the Preparative Utility of N-(silyalkyl)phthalimide and N-(silylalkyl)maleimide photochemistry", pp. 4411-4418 (see abstract).
CAPLUS Abstract Accession No. 1998: 352139 & JP 1014758 A2 (Fujisawa Pharmaceutical Co. Ltd., Japan) Feb. 6, 1998 (see abstract).
CAPLUS Abstract Accession No. 1996:446320 & JP 08092258A2 (Mitsui Petrochemical Ind, Japan) Sep. 4, 1996 (see abstract).

(Continued)

Primary Examiner—Sikarl A Witherspoon

(57) ABSTRACT

The invention provides a process for preparation of a fluorohaloalkane, preferably an [$^{18}$F]fluorohaloalkane of formula (I) wherein X is halo and n is an integer of from 1 to 6; which comprises: reaction of the corresponding organosilicon compound of formula (II): wherein n is as defined for the compound of formula (I); and R', R", and R''' are independently selected from $C_{1-6}$ alkyl and $C_{1-6}$ haloalkyl; and R" may alternatively be the group: with a compound of formula (III): wherein X is as defined for the compound of formula (I) and Y is halo. Intermediates having use in such processes are also claimed.

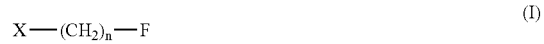

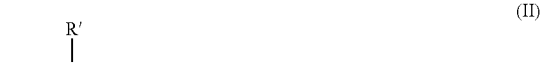

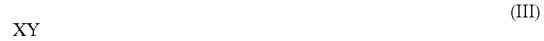

13 Claims, No Drawings

OTHER PUBLICATIONS

CAPLUS Abstract Accession No. 1989:534246 & Journal of the Chemical society, Chemical Communications vol. 17, 1988, Steven L. Jones, et.al., "Protophilic versus silicophilic reactions in β-substituted silanes", pp. 1153-1154 (see abstract).

CAPLUS Abstract Accession No. 1994:30806 & Organometallics vol. 12, No. 12, 1993, Hans Buerger and Peter Moritz, "Novel (fluoromethyl)silicon derivatives from (fluorodibromomethyl) silane precursors", pp. 4930-4939 (see abstract).

CAPLUS Abstract Accession No. 1980:494362 & Collection of Czechoslovak Chemical Communications vol. 45, No. 3, 1980, Marie Jakoubkova, et.al., Organosilicon compounds. CLXVII. Carbon-fluorine bond stretching frequency (ν(C-F)) in some organosilicon compounds, pp. 854-860 (see abstract).

CAPLUS Abstract Accession No. 1977:42771 & Collection of Czechoslovak Chemical Communications vol. 41, No. 9, 1976, J Vcelak, et.al., "Organisilicon compounds. CXLII. The reactivity of fluorine in (ω-fluoroalkyl)-substituted silanes", pp. 2708-2713.

International Search Report for PCT/GB03/04026 dated Mar. 2004.

Search Report for GB 0222426.9 dated Mar. 2003.

Search Report for GB 0222426.9 dated Aug. 2003.

International Preliminary Examination Report for PCT/GB03/04026 dated Jan. 2005.

* cited by examiner

CHEMICAL PROCESS

This application is a filing under 35 U.S.C. 371 of international application number PCT/GB2003/004026, filed Sep. 18, 2003, which claims priority to application number 0222426.9 filed Sep. 27, 2002, in Great Britain the entire disclosure of which is hereby incorporated by reference.

The present invention relates to a process for the preparation of fluorohaloalkane compounds such as [$^{18}$F]bromofluoromethane. [$^{18}$F]Fluorohaloalkanes are important reagents for performing O—, N—, and S—[$^{18}$F]fluoroalkylations and are commonly used to radiolabel radioligands for use in positron emission tomography (PET) studies.

[$^{18}$F]Fluorohaloalkanes have previously been prepared by nucleophilic displacement, by [$^{18}$F]F$^-$, of a leaving group from a suitable precursor compound.

Thus, for example Zhang et al, Applied Radiation and Isotopes 57, 335-342 (2002), describes synthesis of [$^{18}$F]fluoroethyl bromide by nucleophilic displacement of 2-trifluoromethanesulphonyloxy ethylbromide with [$^{18}$F]F$^-$ and Seung-Jun et al Applied Radiation and Isotopes (1999), 51, 293-7 describes an analogous synthesis of 3-[$^{18}$F]fluoropropylbromide. A similar method is described in Comagic et a Applied Radiation and Isotopes (2002), 56, 847-851 wherein 2-bromo-1-[$^{18}$F]fluoroethane is prepared by nucleophilic displacement of 1,2-dibromoethane with [$^{18}$F]F$^-$.

In view of the importance of [$^{18}$F]Fluorohaloalkanes as radiolabelling reagents, there exists the need for synthetic methods for their preparation in good radiochemical yield and in which isolation of the product is more readily achievable. Furthermore, there is also a need for such synthetic methods which are amenable to automation.

Therefore, according to the present invention, there is provided a process for preparation of a fluorohaloalkane of formula (I)

   (I)

wherein X is halo and n is an integer of from 1 to 6; which comprises:
reaction of the corresponding organosilicon compound of formula (II):

   (II)

wherein n is as defined for the compound of formula (I); and R', R", and R'" are independently selected from $C_{1-6}$ alkyl and $C_{1-6}$ haloalkyl; and
R" may alternatively be the group:

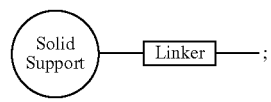

with a compound of formula (III):

   (III)

wherein X is as defined for the compound of formula (I) and Y is halo.

In a preferred aspect of the invention, the fluorohaloalkane of formula (I) is a [$^{18}$F]fluorohaloalkane. Therefore, according to a further aspect of the present invention, there is provided a process for preparation of a [$^{18}$F]fluorohaloalkane of formula (Ia)

   (Ia)

wherein X is halo and n is an integer of from 1 to 6; which comprises:
reaction of the corresponding organosilicon compound of formula (IIa):

   (IIa)

wherein n is as defined for the compound of formula (Ia); and R', R", and R'" are independently selected from $C_{1-6}$ alkyl and $C_{1-6}$ haloalkyl; and
R" may alternatively be the group:

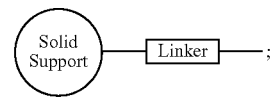

with a compound of formula (III):

   (III)

Examples of formula (I) which may be prepared using the present process, include fluorobromomethane, fluoroiodomethane, fluorobromoethane, fluoroiodoethane, fluorobromopropane, and fluoroiodopropane, each of which is suitably prepared in [$^{18}$F]-labelled form.

The reaction of a compound of formula (II) or (IIa) with a compound of formula (III) may be performed in the presence of a catalyst, suitably a tetra ($C_{1-6}$ alkyl) ammonium salt, such as a tetra ($C_{1-6}$ alkyl) ammonium fluoride salt, for example tetrabutylammonium fluoride or tetraethylammonium fluoride; and in a suitable solvent for example acetonitrile or an alcohol such as methanol or ethanol at elevated temperature, for example 50° C. to 150° C., suitably 70° C. to 120° C.

The resulting compound of formula (I) or (Ia) may be isolated from the reaction mixture, for example, by distillation followed by chromatography, suitably gas or liquid chromatography. In a preferred isolation method, the crude reaction mixture is distilled and the distillate is then passed under a stream of inert gas, such as helium, through a temperature controlled GC column packed with silica gel.

The resulting compound of formula (I) or (Ia) may also be converted to a corresponding fluoroalkylsulphonyl ester of formula (V) or (Va) respectively:

   (V)

   (Va)

wherein n is as defined for the compound of formula (I) or (Ia), and R$^1$ is selected from $C_{1-6}$ alkyl (for example, methyl), $C_{1-6}$ perfluoroalkyl (for example, trifluoromethyl), aryl (for example, phenyl), tolyl (for example, para-tolyl), perfluoroaryl (for example, perfluorophenyl), and perfluorotolyl (for example, perfluoro para-tolyl). Thus, for example a [$^{18}$F]fluorohaloalkyl compound of formula (Ia) may be converted to a [$^{18}$F]fluoroalkyltosylate of formula (Va) such as [$^{18}$F]fluoromethyltosylate. Fluoroalkylsulphonyl esters of formulae (V) and (Va) are also useful as fluoroalkylating agents.

Conversion of a compound of formula (I) or (Ia) to a compound of formula (V) or (Va) respectively, may be effected by reaction with the appropriate sulphonic acid of formula R$^1$SO$_2$OH or a salt thereof, such as a silver salt. Depending on the particular compound to be prepared, this conversion may be performed in solution phase, or in gaseous phase, for example by methods analogous to those described by Iwata et al., Applied Radiation and Isotopes, 57 (2002), 347-352.

The resulting compound of formula (I) or (Ia), or a corresponding compound of formula (V) or (Va) as described above, may be used in the preparation of a fluoroalkyl ligand or radiotracer, for example a [$^{18}$F]fluoroalkylated radioligand or [$^{18}$F]-radiotracer suitable for use in a PET study. Examples of [$^{18}$F]fluoroalkylated radioligands and [$^{18}$F]-radiotracers which may be prepared using the compounds of formula (Ia) or (Va) include 2-(1,1-dicyanopropen-2-yl)-6-(2-[$^{18}$F]-fluoroC$_{1-6}$alkyl)-methylamino)naphthalene (for example, 2-(1,1-dicyanopropen-2-yl)-6-(2-[$^{18}$F]-fluoroethyl)-methylamino)naphthalene, FDDNP), 3-(2'-[$^{18}$F]fluoroC$_{1-6}$alkyl) spiperone (for example 3-(2'-[$^{18}$F]fluoroethyl)spiperone), [$^{18}$F][2-fluoroC$_{1-6}$-alkoxy-5-(5-trifluoromethyl-tetrazol-1-yl)-benzyl]-([2S,3S]-2-phenyl-piperidin-3-yl)-amine (for example, [$^{18}$F][2-fluoromethoxy-5-(5-trifluoromethyl-tetrazol-1-yl)-benzyl]-([2S,3S]-2-phenyl-piperidin-3-yl)-amine), 2-beta-carbomethoxy-3-beta-(4-iodophenyl)-8-(3-[$^{18}$F]fluoroC$_{1-6}$alkyl)-nortropane (for example, 2-beta-carbomethoxy-3-beta-(4-iodophenyl)-8-(3-[$^{18}$F]fluoropropyl)-nortropane, [$^{18}$F]fluoroC$_{1-6}$alkylflumazenil (for example, [$^{18}$F]fluoroethylflumazenil), [$^{18}$F]fluoroC$_{1-6}$alkyl-choline (for example, [$^{18}$F]fluoromethyl-choline or [$^{18}$F]fluoroethyl-choline), O-2 [$^{18}$F]fluoroalkyl tyrosine (for example O-2[$^{18}$F]fluoroethyl tyrosine or O-2[$^{18}$F]fluoropropyl tyrosine), and 1-amino-3 [$^{18}$F]-fluoroalkylcyclobutane-1-carboxylic acid (for example, 1-amino-3-[$^{18}$F]-fluoromethylcyclobutane-1-carboxylic acid, (FMACBC)). Other [$^{18}$F]fluoroalkylated radioligands and [$^{18}$F]-radiotracers which may be prepared using the compounds of formula (Ia) or (Va) include [$^{18}$F]-benzyl derivatives.

In the compounds of formulae (I), (Ia), (II), and (IIa), n is preferably 1, 2, or 3 such that the fluorohaloalkane prepared in the process is a fluorohalomethane, fluorohaloethane, or fluorohalopropane.

Throughout the specification, the term "halo" means fluoro, chloro, iodo, or bromo.

In the compounds of formulae (I), (Ia), and (III), X is halo, and is preferably bromo or iodo.

In the compounds of formula (III), Y is halo, preferably bromo or iodo, and is preferably the same as X, such that the compound of formula (III) is preferably Br$_2$ or I$_2$.

In the compounds of formula (II) and (IIa), R', R'', and R''' are suitably selected from C$_{1-6}$alkyl and C$_{1-6}$haloalkyl, more suitably C$_{1-4}$alkyl and C$_{1-4}$haloalkyl, for example methyl, ethyl, propyl, and isopropyl, typically methyl.

Where R'' is the group:

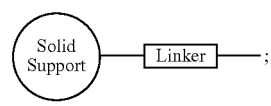;

the "Solid Support" may be any suitable material which is insoluble in any solvents to be used in the process but to which the "Linker" and/or compound of formula (II) or (IIa) can be covalently bound. Examples of suitable solid support include polymers such as polystyrene (which may be block grafted, for example, with polyethylene glycol), polyacrylamide, and polypropylene or glass or silicon suitably coated with such a polymer. The solid support may be in the form of small discrete particles such as beads or pins, or as a coating on the inner surface of a cartridge or on a microfabricated vessel; and the "Linker" may be any suitable organic group which serves to space the reactive site sufficiently from the solid support structure so as to maximise reactivity. Suitably, the Linker comprises an organic group of from 1 to 12 carbon atoms and from 0 to 6 heteroatoms selected from oxygen, nitrogen, and sulphur. Examples of such linkers are well known to those skilled in the art of solid-phase chemistry, but include phenyl(C$_{1-6}$alkyl) and phenyl.

Certain of the compounds of formula (II) and (IIa) are novel and thus form a separate aspect of the invention.

Accordingly, there is provided a compound of formula (II):

wherein n is an integer of from 1 to 6; and

R' and R''' are independently selected from C$_{1-6}$alkyl and C$_{1-6}$haloalkyl; and R'' is the group:

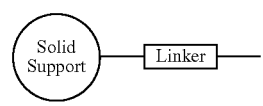

Further, there is provided a compound of formula (IIa):

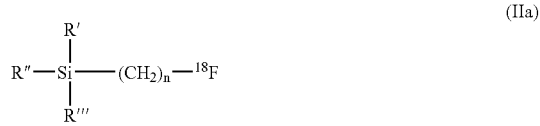

wherein n is an integer of from 1 to 6; and

R', R'', and R''' are independently selected from C$_{1-6}$alkyl and C$_{1-6}$haloalkyl; and R'' may alternatively be the group:

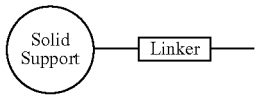

Compounds of formula (II) or (IIa) may be prepared from the corresponding compound of formula (IV):

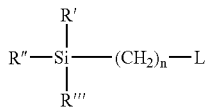

wherein n, R', R", and R''' are as defined for the compound of formula (II) or (IIa) and L is a leaving group;
by reaction with a source of F⁻, preferably $^{18}$F⁻, suitably an alkali metal fluoride salt such as Na$^{18}$F⁻, K$^{18}$F, or Cs$^{18}$F, tetraalkylammonium $^{18}$F fluoride, or tetraalkylphosphonium $^{18}$F fluoride;
in the presence of a phase transfer catalyst, suitably 18-crown-6 or a cryptand such as Kryptofix 2.2.2., Kryptofix 2.2.2B., Kryptofix 2.2.1. (all available from Aldrich). The reaction may be performed in a suitable solvent such as acetonitrile and at elevated temperature, suitably 50° C. to 100° C.

The leaving group, L, in the compound of formula (IV) is suitably a sulphonyl ester group i.e. —OSO$_2$R$^2$ wherein R$^2$ is selected from C$_{1-6}$ alkyl (for example, methyl), C$_{1-6}$ perfluoroalkyl (for example, trifluoromethyl), aryl (for example, phenyl), tolyl (for example, para-tolyl), perfluoroaryl (for example, perfluorophenyl), and perfluorotolyl (for example, perfluoro para-tolyl).

Certain of the compounds of formula (IV) are novel, and therefore according to a further aspect of the invention there is provided a compound of formula (IV):

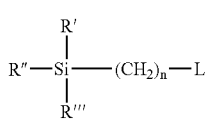

wherein n is an integer of from 1 to 6;
R', R", and R''' are independently selected from C$_{1-6}$ alkyl and C$_{1-6}$ haloalkyl; and
R" may alternatively be the group:

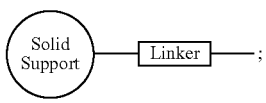

L is a group —OSO$_2$R$^2$ wherein R$^2$ is selected from C$_{1-6}$ alkyl, C$_{1-6}$ perfluoroalkyl, aryl, perfluoroaryl, tolyl, and perfluorotolyl;
provided that:
(a) when R" is C$_{1-6}$ alkyl or C$_{1-6}$ haloalkyl, n is not 1; and
(b) when R" is C$_{1-6}$ alkyl or C$_{1-6}$ haloalkyl and n is 2 to 6, L is not —OSO$_2$CH$_3$ or —OSO$_2$(para-methyl)phenyl.

Compounds of formula (IV) in which R" is the group

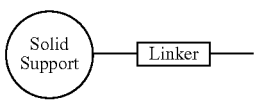

are a particularly useful class of intermediates and thus form a separate aspect of the invention.

Compounds of formula (IV) are either commercially available (for example, from Aldrich), or a readily prepared from commercially available starting materials using methods available to the person skilled in the art. In one suitable method, the compound of formula (IV) is prepared by reaction of the corresponding azide with the appropriate sulphonic acid or a salt thereof, for example using methods analogous to those described in Al-Busafi et al., Tetrahedron Letters, 39, 12 (1998).

The invention will now be illustrated by way of the following Example.

EXAMPLE

Preparation of [$^{18}$F]fluorobromomethane

Trimethylsilylmethyl trifluoromethanesulphonate (Aldrich) (5 mg) in acetonitrile (1 ml) was added to fully dried $^{18}$F⁻/Kryptofix 2.2.2 complex prepared by standard methods, for example as described in Hammacher et al, J. Nuclear Medicine, 27, 235-8 (1986). The mixture was heated at 75° C. for 5 minutes. Tetrabutylammonium fluoride (16 mg) in acetonitrile (0.5 ml) and bromine (8 mg) in methanol (0.5 ml) were added to the reaction mixture. The reaction vessel was then sealed and heated at 110° C. for 3 to 4 minutes.

[$^{18}$F]fluorobromomethane produced was then distilled from the vessel at the same temperature. The distillate containing [$^{18}$F]fluorobromomethane was passed under a stream of helium through a temperature controlled GC column (7.8× 80 mm) packed with silica gel (70 to 270 mesh, Aldrich). The output from the GC column was examined by a radioactive detector and the fraction with a retention time identical to that of authentic bromofluoromethane was directed to a cooled trapping vial containing a suitable solvent. Suitable solvents include acetonitrile, N,N-dimethylformamide, dimethylsulphoxide, tetrahydrofuran, acetone, acetic acid, and chlorobenzene. Other fractions were vented to waste. The overall radiochemical yield for [$^{18}$F]fluorobromomethane from [$^{18}$F] fluoride was 55-70% and the total time for the preparation was approximately 45 minutes from the end of radionuclide production.

What is claimed is:
1. A process for preparation of a fluorohaloalkane of formula (I)

wherein X is halo and n is an integer of from 1 to 6; which comprises:
reacting an organosilicon compound of formula (II):

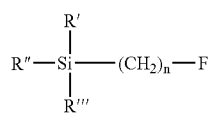

wherein n is as defined for the compound of formula (I); and
R', R", and R'" are independently $C_{1-6}$ alkyl or $C_{1-6}$ haloalkyl; and
R" may alternatively be the group:

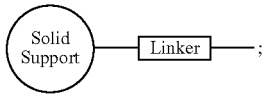

with a compound of formula (III):

$$XY \qquad (III)$$

wherein X is as defined for the compound of formula (I) and Y is halo.

2. A process according to claim 1 for preparation of a [$^{18}$F]fluorohaloalkane of formula (Ia)

$$X—(CH_2)_n—{}^{18}F \qquad (Ia)$$

wherein X is halo and n is an integer of from 1 to 6; which comprises:
reacting an organosilicon compound of formula (II):

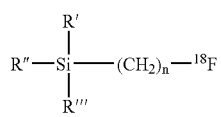

(IIa)

wherein n is as defined for the compound of formula (Ia); and
R', R", and R'" are independently $C_{1-6}$ alkyl or $C_{1-6}$ haloalkyl; and
R" may alternatively be the group:

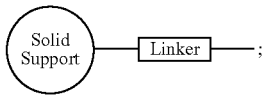

with a compound of formula (III):

$$XY \qquad (III)$$

wherein X is as defined for the compound of formula (Ia) and Y is halo.

3. A process according to claim 1 which comprises the further step:
(i) isolating the compound of formula (I); and/or
(ii) converting the compound of formula (I) to a corresponding fluoroalkylsulphonyl ester of formula (V):

$$R^1SO_2—O—(CH_2)_n—F \qquad (V)$$

wherein n is as defined for the compound of formula (I), and $R^1$ is $C_{1-6}$ alkyl, $C_{1-6}$ perfluoroalkyl, aryl, tolyl, perfluoroaryl, or perfluorotolyl.

4. A process according to claim 1 which comprises the further step:
(i) preparing a fluoroalkyl ligand or radiotracer from the compound of formula (I).

5. A process according to claim 2 which comprises the further step:
(i) preparing a fluoroalkyl ligand or radiotracer from the compound of formula (Ia).

6. The process according to claim 5, wherein:
the fluoroalkyl ligand or radiotracer is a [$^{18}$F]fluoroalkylated radioligand or [$^{18}$F]-radiotracer.

7. A process according to claim 6 wherein the radioligand or radiotracer prepared is:
2-(1,1-dicyanopropen-2-yl)-6-(2-[$^{18}$F]-fluoroC$_{1-6}$alkyl)-methylamino)naphthalene,
3-(2'-[$^{18}$F]fluoroC$_{1-6}$alkyl)spiperone,
[$^{18}$F][2-fluoroC$_{1-6}$alkoxy-5-(5-trifluoromethyl-tetrazol-1-yl)-benzyl]-([2S,3S]-2-phenyl-piperidin-3-yl)-amine,
2-beta-carbomethoxy-3-beta-(4-iodophenyl)-8-(3[$^{18}$F]fluoroC$_{1-6}$alkyl)-nortropane,
[$^{18}$F]fluoroC$_{1-6}$alkylflumazenil, or
[$^{18}$F]fluoroC$_{1-6}$alkyl-choline.

8. A process according to claim 6 wherein the [$^{18}$F]fluoroalkylated radioligand prepared is:
2-( 1,1-dicyanopropen-2-yl)-6-(2-[$^{18}$F]-fluoroethyl)-methylamino)naphthalene,
3-(2'-[$^{18}$F]fluoroethyl)spiperone,
[$^{18}$F][2-fluoromethoxy-5-(5-trifluoromethyl-tetrazol-1-yl)-benzyl]-([2S ,3S]-2-phenyl-piperidin-3-yl)-amine),
2-beta-carbomethoxy-3-beta-(4-iodophenyl)-8-(3-[$^{18}$F]fluoropropyl)-nortropane,
[$^{18}$F]fluoroethylflumazenil),
[$^{18}$F]fluoromethyl-choline, or
[$^{18}$F]fluoroethyl-choline).

9. A process for the preparation of a compound of formula (IIa) as defined in claim 2 which comprises reacting a compound of formula (IV):

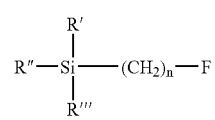

(IV)

wherein n, R', R", and R'" are as defined for the compound of formula (IIa), and L is a leaving group;
with a source of $^{18}$F$^-$ in the presence of a phase transfer catalyst.

10. A compound of formula (II):

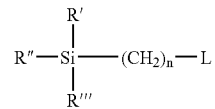

(II)

wherein n is an integer of from 1 to 6; and
R' and R'" are independently $C_{1-6}$ alkyl or $C_{1-6}$ haloalkyl; and
R" is the group:

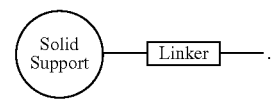

11. A compound of formula (IIa):

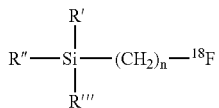
(IIa)

wherein n is an integer of from 1 to 6; and
R', R", and R''' are independently $C_{1-6}$ alkyl or $C_{1-6}$ haloalkyl; and
R" may alternatively be the group:

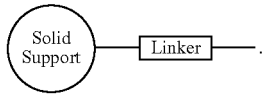

12. A compound of formula (IV):

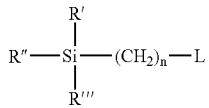
(IV)

wherein n is an integer of from 1 to 6;

R', R", and R''' are independently $C_{1-6}$ alkyl or $C_{1-6}$ haloalkyl; and R" may alternatively be the group:

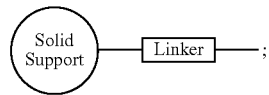

L is a group $-OSO_2R^2$ wherein $R^2$ is $C_{1-6}$ alkyl, $C_{1-6}$ perfluoroalkyl, aryl, perfluoroaryl, tolyl, or perfluorotolyl;

provided that:
(a) when R" is $C_{1-6}$ alkyl or $C_{1-6}$ haloalkyl, n is not 1; and
(b) when R" is $C_{1-6}$ alkyl or $C_{1-6}$ haloalkyl and n is 2 to 6, L is not $-OSO_2CH_3$ or $-OSO_2$(para-methyl)phenyl.

13. A process according to claim 2 which comprises the further step:
(i) isolating the compound of formula (Ia); and/or
(ii) converting the compound of formula (Ia) to a corresponding fluoroalkylsulphonyl ester of formula (Va):

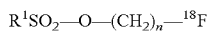
(Va)

wherein n is as defined for the compound of formula (Ia), and $R^1$ is $C_{1-6}$ alkyl, $C_{1-6}$ perfluoroalkyl, aryl, tolyl, perfluoroaryl, or perfluorotolyl.

* * * * *